United States Patent
Pinsky et al.

(10) Patent No.: US 9,901,066 B2
(45) Date of Patent: Feb. 27, 2018

(54) SYSTEM AND METHOD FOR TREATING LIVESTOCK

(71) Applicant: Afimilk Agricultural Cooperative Ltd., Kibutz Afikim (IL)

(72) Inventors: Niv Pinsky, Kibbutz Afikim (IL); Efraim Garti, Zichron Yaakov (IL); Itamar Cohen, Givat Yoav (IL)

(73) Assignee: Afimilk Agricultural Cooperative Ltd., Kibbutz Afikim (IL)

( * ) Notice: Subject to any disclaimer, the term of this patent is extended or adjusted under 35 U.S.C. 154(b) by 0 days.

(21) Appl. No.: 15/354,579

(22) Filed: Nov. 17, 2016

(65) Prior Publication Data

US 2017/0064919 A1    Mar. 9, 2017

Related U.S. Application Data

(63) Continuation of application No. 14/215,677, filed on Mar. 17, 2014, now Pat. No. 9,497,926.

(51) Int. Cl.
| | |
|---|---|
| *A01J 5/003* | (2006.01) |
| *A01K 13/00* | (2006.01) |
| *A01J 5/017* | (2006.01) |
| *A61B 5/00* | (2006.01) |
| *A61D 17/00* | (2006.01) |

(Continued)

(52) U.S. Cl.
CPC ............ *A01J 5/003* (2013.01); *A01J 5/0175* (2013.01); *A01J 7/02* (2013.01); *A01J 7/04* (2013.01); *A01K 1/126* (2013.01); *A01K 13/001* (2013.01); *A01K 29/005* (2013.01); *A61B 5/0077* (2013.01); *A61B 5/01* (2013.01); *A61B 5/02411* (2013.01); *A61B 5/117* (2013.01); *A61B 8/0866* (2013.01); *A61D 17/006* (2013.01); *B25J 5/007* (2013.01); *B25J 11/0045* (2013.01); *A61B 5/6893* (2013.01); *A61B 8/02* (2013.01); *A61B 2503/02* (2013.01); *A61B 2503/40* (2013.01); *Y10S 901/01* (2013.01); *Y10S 901/47* (2013.01)

(58) Field of Classification Search
CPC .. A01J 5/003; A01J 5/0175; A01J 7/02; A01J 7/04; A01K 1/123; A01K 1/126
USPC ...................................................... 119/14.02
See application file for complete search history.

(56) References Cited

U.S. PATENT DOCUMENTS

| | | | |
|---|---|---|---|
| 7,640,889 B2 * | 1/2010 | Van Den Berg | ........ A01J 5/003 119/14.14 |
| 2003/0154925 A1 * | 8/2003 | Van Den Berg | ........ A01J 5/003 119/14.02 |

(Continued)

OTHER PUBLICATIONS

International Search Report for Application No. PCT/IL2015/050194, dated Jun. 7, 2015.

*Primary Examiner* — Joshua D Huson
(74) *Attorney, Agent, or Firm* — Pearl Cohen Zedek Latzer Baratz LLP

(57) ABSTRACT

A system and method for treating livestock may include a ramp for containing dairy livestock and one or more mobile units configured to travel on the ramp, below the dairy livestock, and perform at least one action related to a treatment of the livestock. A mobile unit may be adapted to travel to a predefined location within a stall, and attach a milking equipment unit to a cow in the stall. A plurality of mobile units and a central management unit may be configured to dynamically cause at least some of the plurality of mobile units to each perform a portion of a treatment or task.

5 Claims, 2 Drawing Sheets

(51) Int. Cl.

| | |
|---|---|
| *A61B 5/024* | (2006.01) |
| *A01J 7/02* | (2006.01) |
| *A61B 8/08* | (2006.01) |
| *A61B 5/01* | (2006.01) |
| *A01K 1/12* | (2006.01) |
| *A01J 7/04* | (2006.01) |
| *A01K 29/00* | (2006.01) |
| *A61B 5/117* | (2016.01) |
| *B25J 5/00* | (2006.01) |
| *B25J 11/00* | (2006.01) |
| *A61B 8/02* | (2006.01) |

(56) References Cited

U.S. PATENT DOCUMENTS

| | | | |
|---|---|---|---|
| 2005/0076839 A1* | 4/2005 | Van Den Berg | A01J 5/017 119/14.04 |
| 2005/0115506 A1* | 6/2005 | Van Den Berg | A01J 5/017 119/14.03 |
| 2009/0308327 A1* | 12/2009 | Van Den Berg | A01K 1/01 119/518 |
| 2012/0210938 A1* | 8/2012 | Hofman | A01J 7/04 119/14.02 |

* cited by examiner

SYSTEM AND METHOD FOR TREATING LIVESTOCK

CROSS REFERENCE TO RELATED APPLICATIONS

This application is a continuation application of U.S. patent application Ser. No. 14/215,677, now U.S. Pat. No. 9,497,926, filed on Mar. 17, 2014, which is incorporated herein by reference.

FIELD OF THE INVENTION

The present invention is in the field treating livestock. In particular, the present invention is directed to milking, disinfecting and other treatment of dairy livestock.

BACKGROUND OF THE INVENTION

Automated systems for treating dairy livestock are known. For example, robotic milking machines are known. Typically, a milking robot comprises an arm that attaches a milking unit to a cow (or other dairy livestock). Other operations of a milking robot arm may include removing a milking unit from a cow, placing the milking unit in a housing etc.

However, known systems and methods suffer from a number of drawbacks. For example, the arm of a milking robot travels relatively long distances and covers large spaces. For example, in order to attach a milking unit to a cow, the arm needs to enter (and exit) the stall containing the cow.

SUMMARY OF THE INVENTION

Embodiments of the invention may include a system and method for treating livestock. In particular, embodiments of the invention may include a system and method directed to milking, disinfecting and other treatment of dairy livestock. An embodiment of a system may include a ramp for containing dairy livestock and one or more mobile units configured to travel on the ramp, below the dairy livestock, and perform at least one action related to a treatment of the dairy livestock.

An action performed by a mobile unit may be, or may include, milking, disinfecting, cleaning the ramp, washing the livestock, acquiring an image, identifying the livestock, testing for pregnancy, capturing a heartbeat of a fetus and heating an organ of the livestock.

An embodiment of a system may include ramp adapted to translate both the livestock and the mobile unit. An embodiment of a system may include ramp configured to house a milking equipment unit and a mobile unit may be adapted to detach the milking equipment unit from a housing and attach the milking equipment unit to dairy livestock.

A mobile unit may be adapted to determine its location and, based on its location, determine a location of a milking equipment unit. A plurality of mobile units and a central management unit may be configured to dynamically cause at least some of the plurality of mobile units to each perform a portion of a treatment or task. A first mobile unit may be adapted to attach a first portion of a milking unit to the dairy livestock and a second mobile unit may be adapted to attach a second portion of the milking equipment to the dairy livestock.

An embodiment of a system may include ramp that includes a guide designed to keep the mobile unit within a predefined path under the livestock. An embodiment of a system may include a ramp that includes stalls and a mobile unit may be adapted to automatically travel from a first stall to a second stall. A ramp may include a mark and a mobile unit may be adapted to use the mark in order to determine its location with respect to a stall. A mobile unit may be configured to travel between legs of the livestock.

An embodiment of a system may include a maintenance pit for servicing mobile units. A mobile unit may travel from a guide to a service or maintenance pit. A first mobile unit may be adapted or caused complete an action which at least one other mobile unit failed to complete. A mobile unit may include sensors and/or treatment units.

An embodiment of a system may include a central management unit adapted to instruct or cause a mobile unit to perform an action. An embodiment of a system may include a set of mobile units configured to inter-communicate in order to collaborate in performing an action related to treatment of the livestock.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

Figure 1:
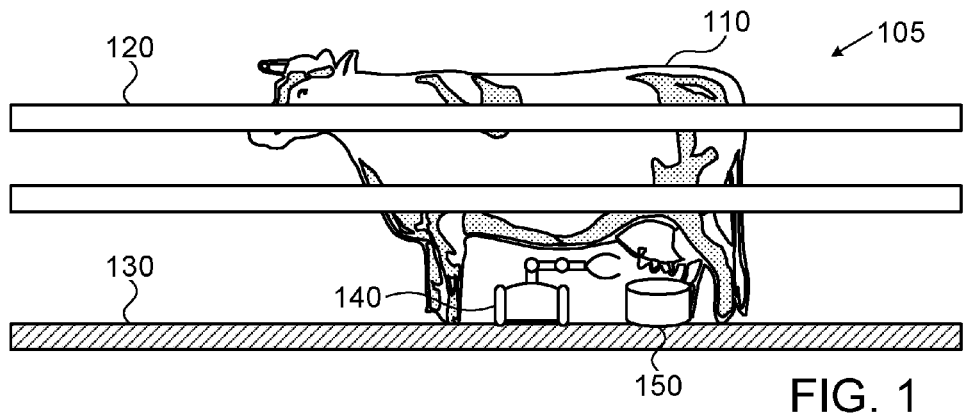
FIG. 1 shows an exemplary system according to embodiments of the invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory processor-readable storage medium that may store instructions, which when executed by the processor, cause the processor to perform operations and/or processes.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Although embodiments of the invention are not limited in this regard, the term "set" when used herein may include one or more items.

Although dairy livestock (and in particular, cows) are mainly discussed herein, it will be understood that embodiments of the invention may be applicable to any type of livestock (e.g., goats, sheep, horses etc.). Although milking of dairy livestock is mainly discussed herein it will be understood that embodiments of the invention may be applicable to other operations, or treatments of livestock. For example, treatments such as disinfecting or washing the livestock, heating an organ of the livestock and/or milking may all be enabled or performed by a system or method according to embodiments of the invention. Embodiments of the invention may be applicable to operations such as; acquiring an image, testing for pregnancy or capturing a heartbeat of a fetus and/or identifying the livestock.

Reference is made to FIG. 1 that shows an exemplary system 105 according to embodiments of the invention. As shown by FIG. 1, system 105 may include a walkway or ramp 130, an enclosure, fence or stall 120 for containing livestock (e.g., containing cow 110 as shown), a milking unit 150 and a mobile unit 140. In embodiment, mobile unit 140 may be a mobile robot designed to travel on ramp 130 and under the livestock (e.g., under cow 110 as shown in FIG. 1). For example, mobile unit 140 may be designed and manufactured such that it freely travels under, and between the legs of, the livestock.

Various models of mobile unit 140 may be contemplated, for example, a model used for goats may be smaller than one used for cows. In one embodiment, mobile unit 140 is adapted for treating cows. Assuming a space of up to 60 centimeters in height is available under an average cow, mobile unit 140, including an attached arm, may be designed such that it can freely travel through a space that is 50 centimeters in height. Mobile unit 140 may be designed such that it can travel between the fore and hind legs of a cow. Accordingly, mobile unit 140 may small enough in size and may travel under cows standing on a ramp as described.

Including a small mobile unit 140 as described, embodiments of the invention enable advantages which that cannot be achieved by system and methods known in the art. As discussed above, robotic milking machines known in the art use an arm that is based (or extends from) outside the stall containing the livestock. In operation, such arm needs to extend into the stall and under the livestock, e.g., in order to attach a milking unit. An arm extending from outside the stall may harm the livestock when traveling since its path may collide with the livestock, e.g., the legs of a cow in the stall. Moreover, the distance traveled by an arm based (or extending from) outside the stall is relatively long.

Designed to fit, and operate, under the livestock, and travel between the legs of the livestock, mobile unit 140 as described herein eliminates some of the above mentioned drawbacks. For example, as further described herein, mobile unit 140 may travel to a location under the livestock from the side of the livestock, thus, entering a location between the fore and hind legs along a path does not collide with the legs of the livestock.

Embodiments of the invention enable treating livestock by a system that minimizes the movement or distance traveled by an arm. For example, movement of arm 210 may be minimal, e.g., extending from under the cow to a housing of a milking unit that may be in close proximity.

Figure 2:
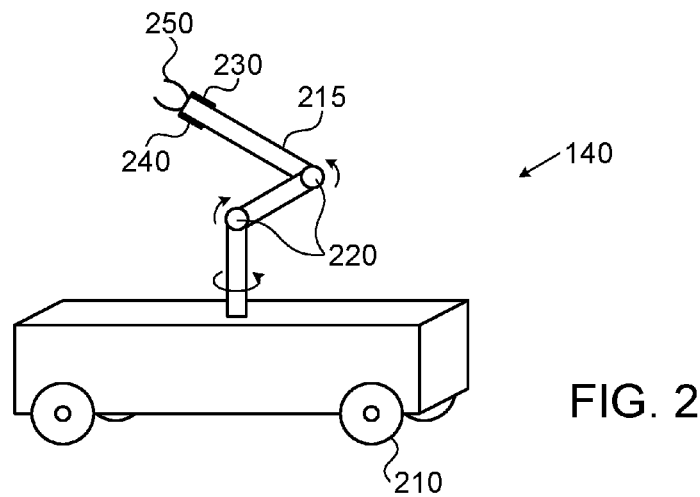
FIG. 2 schematically shows a mobile unit according to embodiments of the invention.

Reference is made to FIG. 2, schematically showing a mobile unit 140 according to embodiments of the invention. As shown, mobile unit 140 may include wheels 210 enabling it to travel, e.g., on ramp 130 as described. It will be understood that other means for enabling a mobility of mobile unit 140 may be used. For example, instead of wheels 210, mobile unit 140 may be equipped with continuous tracks (e.g., as used in bulldozers).

As shown, mobile unit 140 may include an arm 215 having joints 220. As shown, arm 215 may include a gripping unit 250, a set of sensor units 230 and a set of treatment units 240. Arm 215 may be designed such that it may extend and rotate such that gripping unit 250, sensor units 230 and treatment units 240 may be placed at a chosen location and/or orientation. For example, although not shown, mobile unit 140 (or arm 215) may include electric motors adapted to move, rotate and/or extend arm 215 such that gripping unit 250, sensor units 230 and treatment units 240 are brought to a selected location and/or orientation.

Gripping unit 250 may be any unit adapted to selectively hold and release an object. For example, gripping unit 250 may be adapted to hold a milking unit (e.g., securely hold an assembly of teat cups used for milking), and, gripping unit 250 may be adapted to release the milking unit (e.g., after the milking unit is attached to a cow).

Sensor units 230 may include any sensing device, system or module. For example, sensing units 230 may include a camera for acquiring an image of an organ of a cow (e.g., in order to identify the cow). In an embodiment of a system, sensing units 230 may include sensors for testing for pregnancy. Testing for pregnancy using an ultrasonic sensor is known in the art. For example, in an embodiment of a system, sensor units 230 include an ultrasonic sensor used in order to test livestock for pregnancy wherein the actual testing may be performed as known in the art. In the same or other embodiment of a system, sensing units 230 may include sensors for capturing a heartbeat of a fetus. Any other sensors may be included in sensors units 230.

Treatment units 240 may include any applicable device, system or module. For example, treatment units 240 may include a washing unit adapted to wash an organ (e.g., washing the udder of a cow before or after milking). For example, mobile unit 140 may include an assembly including a tank or container that contains liquid (e.g., water, solvent or other liquid solution). The assembly may include pipes to run the liquid from the tank to jets on nozzles included in treatment units 240. The assembly may include a pump to force liquids from a liquid container through the pipes and jets.

An assembly included in mobile unit as described herein may be used for cleaning or washing any object. For example, arm 215 may be positioned such that jets in treatment units 240 are directed downwards, at a floor. For example, mobile unit 140 may wash the floor of ramps 130 and 405 described herein.

Sensor units 230 may include a thermometer for determining a temperature of the livestock or a temperature of an organ of a livestock. For example, udder infections may be identified or detected for example by measuring the temperature of the udder. Any data collected by sensor units 230 may be stored on mobile unit 140, may be processed by a controller included in mobile unit 140 as described herein and/or may be sent to a remote computer using communication components included in mobile unit as described herein (e.g., with reference to FIG. 3).

For the sake of simplicity and clarity, various elements that may be included in mobile unit 140 are not shown in FIG. 2. For example, wires providing electric power to arm 215, sensor units 230 and treatment units 240 may be included but are not shown. Other elements, e.g., wires carrying digital data or signals to/from sensor units 230 and treatment units 240 are not shown. Other elements included and not shown may be pipes or conduits used for running liquids (e.g., liquids used for washing or disinfecting). For example, mobile unit 140 may include an assembly including a container that contains disinfectant liquid (e.g., Iodine) and a pump for causing the liquid to be transferred from the tank and sprayed on an udder of a cow through nozzles or jets in a disinfecting unit included in treatment units 240.

Figure 3:
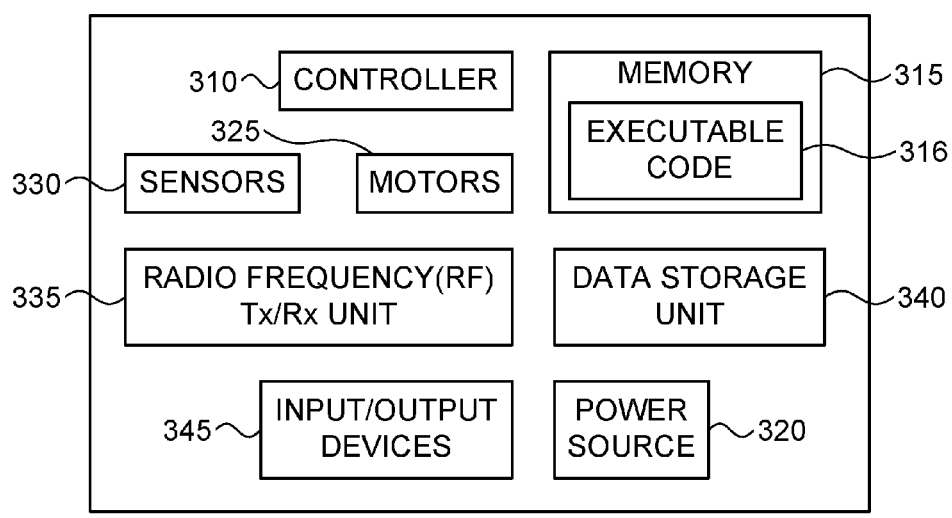
FIG. 3 schematically shows components included in a mobile unit according to embodiments of the invention.

Reference is made to FIG. 3, schematically showing components that may be included in mobile unit 140 according to embodiments of the invention. As shown, mobile unit 140 may include a controller 310, a memory 315, a radio frequency (RF) receive/transmit (Rx/Tx) unit 335 (also referred to as "RF unit 335" herein), a data storage unit 340, input/output (I/O) devices 345, a power source 320, a set of motors 325 and a set of sensors 330. For the sake of simplicity and clarity, some components that may be included in mobile unit 140 are omitted from FIG. 3. For example, arm 215 and wheels 210 are not shown in FIG. 3. Power source may be any suitable power source for providing power to any components of mobile unit 140. For example, power source 320 may be a battery that provides electric energy to motors 325, controller 310, RF unit 335 and/or other components included in mobile unit 140. Accordingly, mobile unit 140 may include an internal power source.

Motors 325 may be electric motors that move arm 215, rotate wheels 210 or drive other components included in mobile unit 140. Sensors 330 may be any suitable sensors. For example, sensors 330 may be adapted to sense light, infra red (IR) light, magnetic flux and the like. For example and as described herein, a sensor included in sensors 330 may sense a mark or markers on path or ramp 130 thus enabling mobile unit 140 to position itself at predefined locations on ramp 130.

RF unit 335 may be a component enabling mobile unit 140 to communicate with any component in a system as described herein. For example, RF unit 335 may be a WiFi (also spelled Wi-Fi or Wifi) component or device enabling mobile unit 140 to communicate with a management system or with other mobile units, e.g., in a system that includes a remote management system and/or a plurality of mobile units 140 as described herein.

Controller 310 may be, for example, a central processing unit processor (CPU), a chip or any suitable computing or computational device. In some embodiments, more than one controller 310 may be used. For example, a plurality of controllers similar to controller 310 may be included in mobile unit 140.

Memory 315 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory or other suitable memory units or storage units. In an embodiment, memory 315 is a non-transitory processor-readable storage medium that stores instructions and the instructions are executed by controller 310. Memory 315 may be or may include a plurality of, possibly different memory units.

Executable code 316 may be any executable code, e.g., an application, a program, a process, software, a task or a script. Executable code 316 may be executed by controller 310 possibly under control of an operating system. For example, executable code 316 may be one or more applications that control or manage components in mobile unit 140. For example, when executed by controller 310, executable code 316 may cause controller 310 to control or manage arm 215, treatment units 240, sensors 230, RF unit 335, motors 325 and other components included in mobile unit 140. Where applicable, executable code 316, when executed by controller 310 may cause controller 310 to carry out operations described herein in real-time. For example, controller 310 may be configured to update, process and/or act upon information at the same rate the information, or a relevant event, are received. Executable code 316 may include a plurality of executable code segments. For example, a first code segment may manage and/or interact with RF unit 335 and a second code segment included in executable code 316 may control motors 325. Executable code 316 may include an operating system (OS) that may a commercial operating system designed and/or configured to perform tasks involving coordination, scheduling, arbitration, supervising, controlling or otherwise managing operation of controller 310, for example, scheduling execution of programs.

Data storage unit 340 may be any suitable system or device capable of storing digital information. For example, data storage unit 340 may include a hard disk, a universal serial bus (USB) device, a CD-Recordable (CD-R) drive and media, a nonvolatile memory chip or any other memory. Content may be stored in data storage unit 340 and may be loaded from data storage unit 340 into memory 315 where it may be processed by controller 310. Content may be stored in data storage unit 340 and may be sent, e.g., using RF unit 335, from data storage unit 340 to a remote computer or system. For example, data acquired by sensor units 230 may be stored in data storage unit 340 and may later be extracted from data storage unit 340 and sent or uploaded to a remote computer.

Input/Output (I/O) devices 345 may be or may include a mouse, a keyboard, a touch screen or pad or any suitable input device. It will be recognized that any suitable number of input devices may be operatively connected to mobile unit 140 or controller 310. I/O devices 345 may include one or more displays, speakers and/or any other suitable output devices. It will be recognized that any suitable number of output devices may be operatively connected to mobile unit 140 or controller 310. Any applicable input/output (I/O) devices may be connected to mobile unit 140 or controller 310. For example, a wired or wireless network interface card (NIC), a modem, printer or facsimile machine, a universal serial bus (USB) device or external hard drive may be included in I/O devices 345.

Embodiments of the invention may include a mini robot (e.g., in the form of mobile unit 140) adapted to travel on a ramp and below dairy livestock. For example, an embodiment of a system may include a mini robot adapted to travel on a ramp on which livestock is standing. An embodiment of a system may include a mini robot adapted to travel to a spot under a cow and park in at the predefined spot, e.g., as further described herein. In an embodiment, the mini robot or mobile unit may carry equipment usable for treating livestock. For example, the mini robot may carry, or extract from a housing, a milking unit and attach the milking unit to a cow. The milking robot may park under the livestock and, when parked, perform a treatment. For example, a treatment may be milking, disinfecting, obtaining measurements and the like. As described, a mini robot or mobile unit may travel on a ramp on which the livestock is standing. For example, a ramp on which cows are standing may include a guide or rail and a mini robot or mobile unit may travel along the guide or rail.

A method of treating dairy livestock may include navigating a mobile unit to a location under the livestock; and carrying out, by the mobile unit, at least one action related to a treatment of the dairy livestock. It will be understood that portions of the operations such as milking, disinfecting, washing and obtaining measurements may include usage of equipment as known in the art. For example, the actual washing of udders of cows as described herein may be done as known in the art. Similarly, using jets to spray a disinfectant liquid may be as known in the art. Accordingly, for the sake of clarity and simplicity, details related to some of the operations performed by a mini robot or mobile unit as described herein are assumed to be understood or known to a person having ordinary skill in the art and are not described in detail.

Figure 4:
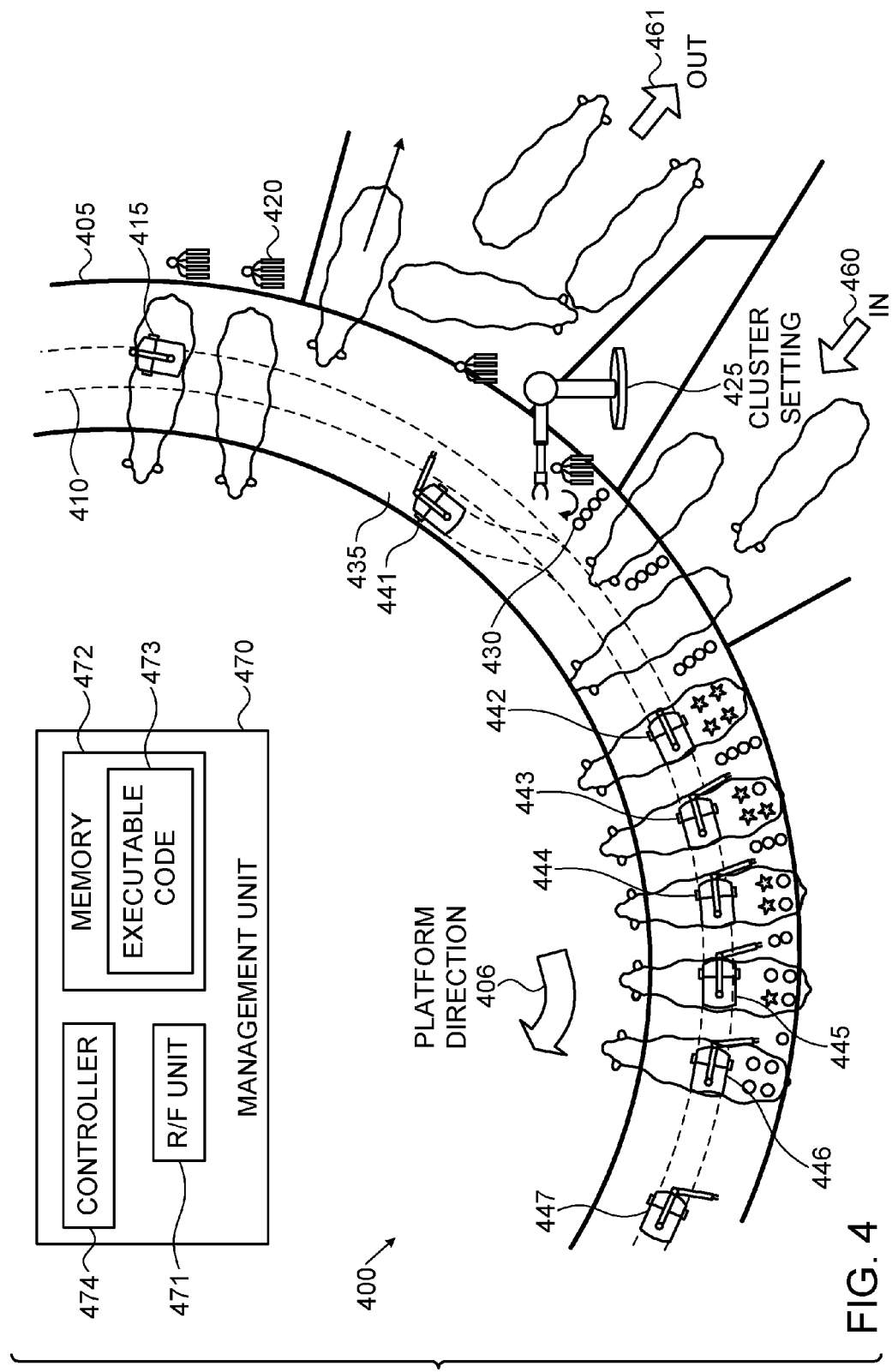
FIG. 4 shows a system according to embodiments of the invention.

Reference is made to FIG. 4 that shows a system 400 according to embodiments of the invention. As described herein, system 400 may be included in or operated as a milking parlor or milking platform. As shown, system 400 may include a ramp 405. For example, ramp 405 may be a platform on which cows stand being milked or treated. As shown by arrow 406, ramp or platform 405 may rotate, with the livestock on it. As shown, ramp 405 may include a guide or rail 410 for guiding mobile units. As shown by mobile units 441, 442, 443, 444, 445, 446, 447 and 415, mobile units that may be similar to mobile unit 140 described herein may be placed on ramp 405 and may travel on ramp 405, e.g., forward or backwards along guide 410 or out to a maintenance pit. As shown system 400 may include a pit 435. For example, as shown by mobile unit 441, a mobile unit may exit guide 410 into a maintenance pit where it may be serviced. As shown by arrow 461, cows may enter or mount ramp 405 through a dedicated opening and as shown by arrow 461, cows may exit ramp 405 through a dedicated opening or gate.

System 400 may include a component for housing a milking unit after milking is completed. For example, as shown by assembly 420, an assembly for housing milking equipment may be included in ramp 405. For example, when placed in assembly 420, a milking unit may be washed, disinfected and the like. A system may include a component for placing milking units in a dedicated place or holder that is relatively close to the location of a cow when milked. For example, as shown by arrangement 430, special holders may be included in ramp 405 and a milking unit may be placed in the holder or holders. For example, quartets of holders 430 may separately hold teat cups. As shown by arm 425, a system may include an arm adapted to extract or fetch a milking unit from assembly 420 and place the milking unit in holders 430. In one embodiment, holders 430 are located at a minimal distance from the cow.

As shown, system 400 may include a management unit 470 that may include an RF unit enabling management unit 470 to communicate with other components of system 400. For example, management unit 470 may communicate with mobile units 441, 442, 443, 444, 445, 446, 447 and 415. As shown, management unit 470 may include a controller or processor 474 and a memory 472 that may include software, instructions or executable code 473. When executed by controller 474, executable code 473 may cause controller 474 to perform operations performed by management unit 470 as described herein. In one embodiment, management unit 470 includes a server computer equipped with RF capabilities. Accordingly, a management software application may be executed on management unit 470 and the management application may communicate with mobile units 441, 442, 443, 444, 445, 446, 447 and 415. Although not shown, management unit 470 may be connected to other components or computers, e.g., management unit 470 may be connected to the internet or to a remote sever. Accordingly, any data obtained by mobile units 441, 442, 443, 444, 445, 446, 447 and 415 may be communicated to management unit 470 and from management unit 470 to any computer or network. Controller or processor 474 and/or controller or processor 310 may be configured to carry out embodiments of the invention by for example executing instructions or software.

As described, a system for treating dairy livestock may include a ramp for containing dairy livestock and one or more mobile units configured to travel on the ramp and below the dairy livestock and perform at least one action related to treatment of the dairy livestock. For example, mobile units 446, 447 and 415 may be small enough to travel under, and between the legs of, cows standing on ramp 405 and may perform various treatments and operations as described herein.

Ramp 405 may be adapted to translate or move both the dairy livestock and the mobile unit. Accordingly, when positioned under a cow, a mobile unit (e.g., mobile unit 442) may be stationary with respect to a cow above it while both the cow and the mobile unit are being translated (e.g., rotated) by ramp 405. For example, ramp 405 may be a round ramp adapted to translate the livestock and mobile units in a circle around a center. Ramp 405 may include stalls (e.g., as shown in FIG. 1) and may rotate slowly such that cows can enter or mount ramp 405 as shown by arrow 460 and exit ramp 405 as shown by arrow 461.

Guide or rail 410 may be designed to keep the mobile units (e.g., mobile units 446, 447 and 415) within a predefined path under the livestock. For example, guide 410 may includes side walls that may prevent mobile units from traveling at any direction other than along guide 410. In one embodiment, guide 410 may include rails on which wheels 210 (that may include a groove that fits the rails) travel such that the rails hold the wheels (and thus the mobile units) in a way similar to the way rails hold or guide a train.

In an embodiment, guide 410 may provide mobile units with electrical energy. For example, contacts may be placed on the sides of guide 410 and may provide current to mobile units via electrical contacts included in mobile units. For example, metal brushes or other components in mobile unit 442 may be connected to motors 325 and be in touch with conductive metal strips or terminals placed on (or along) guide 410. Electric power may be fed into the conductive metal strips or terminals, may flow through the brushes and may power motors 325. Accordingly, guide 410 may provide mobile units with electrical energy.

Mobile unit 140 may be adapted to perform various treatments and operations. For example, mobile unit 415 may disinfect cows (e.g., udders or teats) by spraying a disinfectant liquid. For example, mobile unit 415 may include a container or tank that stores Iodine and treatment units 240 may include a nozzle or jet for spraying the Iodine on cows, e.g., after milking is completed and a milking unit was removed. Treatment units 240 may include a component adapted to warm or heat the udder or other part of a cow, accordingly, a mobile unit as described herein may heat an organ of the livestock, e.g., by attaching a heating component to the livestock.

In one embodiment, a mobile unit (e.g., mobile unit 140) may include a tank or container that stores water or other liquid usable for cleaning or washing the livestock and/or cleaning or washing ramp 405. For example, nozzles included in treatments units 240 may eject water or other liquids on cows standing on ramp 405. Nozzles or jets included in treatments units 240 may be used to wash ramp 405. Acting as a robot, a mobile unit described herein may move arm 215 such that nozzles or jets are directed to wash a livestock or wash ramp 405.

Treatments units 240 and/or sensing units 230 may include a camera usable for acquiring an image. For example, arm 215 may place or aim a camera included in sensing units 230 such that an image of a cow's belly or udder is captured. An image acquired as described may be used for attaching a milking unit (e.g., by determining exact or relevant location of teats). An image may be used to identify a cow. For example, by analyzing an image of an udder or an image of a mark on a cow's belly, the cow may be identified. For example, hot-iron branding on a belly of a cow may be identified by processing an image of the cow's belly and using known image or pattern recognition methods. For example, an image of the cow's belly may be processed by controller 310 or controller 474, a mark may be identified in the processed image and a database that includes a list of the cows and their respective marks may be used in order to identify the cow. Other marks (e.g., made using freeze using liquid nitrogen or dry ice) may be similarly identified. Accordingly, sensing units 230 may include a sensing device for identifying the livestock.

Other devices or sensors included in treatments units 240 and/or sensing units 230 may be devices or sensors for testing for pregnancy as known in the art. For example, an ultrasound sensing device included in sensing units 230 may be used to capture a heartbeat of a fetus.

Any data acquired by sensing units 230 may be stored. For example, images acquired by a camera or signals acquired by a pregnancy sensor may be stored on data storage unit 340. Any data stored on data storage unit 340 may be downloaded or uploaded to a remote computer or data in data storage unit 340 may be communicated over a network. Data in data storage unit 340 may be transferred or copied using a direct wire, e.g., using a USB port included in mobile unit 140. Accordingly, it will be understood that data acquired, processed or generated by mobile units such as 441, 442, 443, 444, 445 and/or 140 may be available to other components of system 400.

In one embodiment, mobile unit 140 (or similar mobile units shown in FIG. 4) may travel to a predefined location under a cow and perform operations described herein when located at the predefined spot or location. For example, an optimal location for treating a cow may be right under the cow, at a short distance from the udder. At the predefined location, mobile unit 140 may rotate or otherwise move or maneuver such it is at a selected orientation. For example, mobile unit 140 may rotate itself such that arm 215 is at minimal distance from holders 430.

To determine its location, mobile unit 140 may use any applicable system or technique. For example, controller 310 (or controller 474) may use image processing techniques in order to determine a location of mobile unit 140, based on video or images received from a camera in sensor units 230.

An electro-mechanic switch may be used in order to enable mobile unit 140 to determine it has reached a predefined spot in a stall. For example, a mechanical sensor included in mobile unit 140 may be configured to detect a mark on guide 410. For example, guide 410 may include a bulge (or cavity or hole) that marks a center of a stall and a rod connected to a micro-switch included in mobile unit 140 may slide along guide 410 and activate the micro-switch when reaching the bulge or cavity. An activation of the micro-switch may enable mobile unit 140 to determine it is located in a center of a stall. An optical sensor included in mobile unit 140 may detect an optically detectable signal emitted from a source placed in a center of a stall. In yet other embodiments, a mark may be or include a magnet placed in a stall and a sensor adapted to sense a change in magnetic flux may be included in mobile unit 140 such that mobile unit 140 may stop or park in a stall based on a sensed magnetic field or flux.

In an embodiment, ramp 130 includes stalls for containing the livestock. For example, when entering platform 405 as shown by arrow 460, cows enter separate stalls.

In an embodiment, the floor of ramp 405 includes markings or marks which are detectable by the mobile units. For example, a mark may be placed at the center of each stall in ramp 130. For example, the mark may be an RF beacon, a specific color, e.g. paint, and the like. A sensor included in sensors 330 may detect a mark (e.g., by identifying the color of the mark or picking up an RF beacon). Based on identifying the location of the mark, mobile unit may travel to a location defined based on the location of the mark. For example, mobile unit may position itself such that it is right above the mark. For example, a sensor included in sensors 330 may send controller 310 the location of a mark (or a relative location with respect to a mobile unit) and controller 310 may cause motors 325 to move (e.g., by driving wheels 210) a mobile unit to a location that is closest to the mark. It will be understood that various other methods or components for enabling a mobile unit to determine its location in a stall may be used.

In an embodiment, a marking or mark may be placed within guide 410. Accordingly, in order to place a mobile unit right above the mark, controller 310 may only need to cause the mobile unit to move in one of two directions (e.g., either forwards or backwards). For example, marks placed on the floor of ramp 405 in guide 410 and at the centers of stalls may be used by mobile units such as 444, 445 and/or 140 in order to determine their location with respect to a stall containing the livestock. For example, using a mark as described, a mobile unit may position itself under a cow in a stall.

As described, a system may include a unit for placing a milking unit in a housing. For example, a system may include an arm 425 adapted to fetch a milking unit from assembly 420 (where the milking units may have been washed or otherwise treated) and place the milking units in holders 430. It will be understood that holders 430 may be any suitable housing adapted to house the milking units.

Holders 430 may be located at a minimal distance from the cow and the location of holder 430, e.g., with respect to a center of a stall, may be known. Accordingly, when located right above a mark, e.g., in a center of a stall, a mobile unit may determine the relative location of holders 430. Accordingly, a mobile unit may be adapted to determine its location (e.g., in a stall) and, based on its location, determine the location of holders 430. Otherwise described, knowing its location in a stall, a mobile unit may readily determine the location of a milking equipment unit housed by holder 430.

In an embodiment, a mobile unit is adapted to detach a milking equipment unit from a housing or holder and attach the milking equipment unit to the dairy livestock. For example, using arm 215 and gripping unit 250, mobile unit 140 may detach a milking unit (e.g., a teat cup) from holders 430 and attach the milking unit to a cow. For example, the location of holders 430 (with respect to a center of a stall) may be known in advance, accordingly, controller 310 may cause arm 215 to move to holders 430 and grip a milking unit. As described, the location and/or shape of an udder may be known to mobile unit 140 (e.g., based on processing an image of the lower part of cow as described). Accordingly, controller 310 may cause arm 215 to move to a location right under an udder and lift teat cups such that they snap onto to the teats (e.g., by force of vacuum in the teat cups as known in the art). It will be noted that when a mobile unit is located right under a cow, the distance an arm of the milking unit needs to travel in order to fetch a milking unit and attached the milking unit to the cow is kept to a minimum. A milking unit may be, for example, a set of four teat cups or it may be one teat cup.

Using marks in stalls as described, a mobile unit may automatically travel from a first stall to a second stall. For example, detecting marks on a floor of ramp 130 as described, mobile units 441, 442, 443, 444, 445, 446, 447 and 415 may travel from a first stall to a second stall. For example, to travel from a first to a second stall, mobile unit 442 may travel, along guide 410 until a mark is detected and determined to be right under mobile unit 442. Leaving a first stall, a mobile unit may travel, along guide 410, till it detects a mark. Detecting a mark on the floor of ramp 130 may indicate to a mobile unit that it is located in the proper position in a stall. In order to travel from a first stall to a third stall, a mobile unit may continue its motion after detecting a first mark till a second mark is detected.

As shown by pit 435, a system may include a service or maintenance pit where mobile units may be parked and serviced. Other operations may be done when a mobile unit is in pit 435, for example, data stored in data storage unit 340 may be transferred or copied from a mobile unit when in pit 435. In an embodiment, management unit 470 may cause a mobile unit to exit guide 410 and enter pit 435. For example, guide 410 may include an arrangement similar to a railroad switch or turnout as used in trains. A turnout may be operated by electric motors that may be controlled by management unit 470 (e.g., using RF or wired communication).

Accordingly, by controlling a component of guide 410, management unit 470 may cause a mobile unit to travel to pit 435, e.g., as shown by mobile unit 441. In an embodiment, management unit 470 may monitor movements and locations of mobile units 441, 442, 443, 444, 445, 446, 447 and 415. For example, mobile units may report their location to management unit 470 or other means may be used (e.g., global positioning system components installed in mobile units). Accordingly, management unit 470 may determine when and how to operate a turnout such that a selected mobile unit travels into the pit.

Mobile units 441, 442, 443, 444, 445, 446, 447 and 415 may collaborate and/or cooperate to complete a task, treatment or operation. As known in the art, a milking unit may include four teat cups that need to be attached to the four teats of a cow. In an embodiment, a first mobile unit (e.g., mobile unit 443) may be adapted to attach a first portion of a milking unit to the dairy livestock and a second mobile unit (e.g., mobile unit 444) may be adapted to attach a second portion of the milking unit to the dairy livestock. For example, mobile unit 443 may attach a first teat cup, mobile unit 444 may attach a second teat cup and mobile units 445 and 446 may respectively attach the third and fourth teat cups. Mobile unit 442 may perform preparation related operations, e.g., washing, heating and the like. As described, by processing an image of an udder, the teats in the udder may be identified and their location may be calculated for example using known computer image processing or recognition methods. For example, if the location of mobile unit 442, when acquiring an image of an udder, is known, and a location of a camera on arm 215 is known (e.g., since the location or position of arm 215 are known) then the location of objects in an image may be calculated. In some embodiments, a video stream may be produced by a camera carried by arm 215 and controller 310 may use a video stream to move arm 215 such that it brings a milking unit to the teats. Any known methods used by robots or other automated systems may be used by mobile units in order to carry and place equipment such as a milking unit at a desired location or position. For example, any methods used by milking robots known in the art may be used by mobile units 415, 442 and 443. As noted, unlike milking robots placed outside a stall, in an embodiment, a milking robot may be or may be included in a small mobile units adapted to move to a location under the livestock and perform operations from under the livestock thus minimizing movement of an arm or other parts of the milking robot.

When a mobile unit completes its task in a current stall it may travel to the next stall, e.g., in a direction opposite to the direction of rotation of ramp 405. Prior to moving to the next stall, a mobile unit may determine whether or not another mobile unit is located in the next stall. For example, as described, management unit 470 may monitor mobile units' locations and may therefore know whether or not mobile unit is located in a specific stall. Accordingly, a mobile unit may communicate with management unit 470 and be advised whether or not it may move from its current stall to the next stall. In another embodiment, a mobile unit may communicate with adjacent mobile units in order to determine their location and thus determine whether or not it may move into a stall. Accordingly, a mobile unit may automatically travel from a first stall to a second stall based on a command or information received from a management unit 470 and/or autonomously, based on information received from other mobile units.

In an embodiment, a plurality of mobile units may be configured to intercommunicate in order to collaborate in performing an action related to treatment of the dairy livestock. Collaboration or cooperation may be realized in various ways. For example, one mobile unit, e.g., mobile unit 442 that may be the first mobile unit to treat a cow in the current milking session, may be include a camera for obtaining an image of the livestock. The image may be processed, e.g., by management unit 470 or by one of the mobile units, and a location of an organ of the livestock may be determined and recorded. For example, using an image and provided with the location of the mobile unit that acquired the image, the location of an udder (and/or teats), with respect to a marking in a stall may be determined and recorded. For example, coordinates of an udder or teats, relative to a mark in a stall may be sent to other mobile units. Accordingly, using an image obtained by mobile unit 442, mobile units 443, 444, 445, 446 and 447 may be informed, in advance, of the location of the udder or teat of the cow.

One (or more) mobile units in a plurality of mobile units may act as a backup unit. For example, in a typical scenario, mobile units 443, 444, 445 and 446 may each attach one of four teat cups to a cow. For example, after mobile unit 443 attaches a first teat cup it moves to the next stall and mobile unit 444 moves to the stall that mobile unit 443 left. Mobile unit 444 may then attach the second of four teat cups to the cow. Thus, mobile units may collaborate in attaching a complete milking assembly.

However, if one of mobile units 443, 444, 445 and 446 fails to attach a teat cup, it may report failure to management unit 470 (or to other mobile units) and mobile unit 447, when acting as a backup unit, may attach a teat cup which another mobile unit failed to attach. Adapted to communicate either with each other or with a central management unit 470, mobile units may send and receive any information related to an operation performed by a set of mobile units. Accordingly, one mobile unit may correct errors or failures caused by another mobile unit. For example, a first mobile unit may automatically complete an action which at least one other mobile unit failed to complete as described.

In an embodiment, each mobile unit in a set of mobile units may be configured to communicate with other mobile units included in the set. A set of mobile units may be configured to dynamically and automatically determine a portion of a treatment to be performed by each of the mobile units in a set. For example, mobile unit 444 may only move to the next stall if mobile unit 443 has left that stall. If mobile unit 444 completes attaching a teat cup as configured and cannot move to the next stall, mobile unit 444 may attach another teat cup, e.g., one typically attached by mobile unit 445. In an embodiment, distribution of sub-tasks may be configured (e.g., each mobile unit is configured to attach one specific teat cup). Mobile units may override a configured distribution of sub-tasks, e.g., a first mobile unit may perform a sub-task that was assigned to a second mobile unit in a configured distribution of sub-tasks.

Mobile units may send any information to management unit. For example, mobile units may report completion of a sub-task, failure to complete a task or sub-task and the like. Management unit 470 may be configured to dynamically cause at least some of the mobile units to each perform a portion of a treatment. For example, provided with information from mobile units related to a progress of a treatment (e.g., milking), management unit 470 may dynamically allocate tasks to mobile units. For example, if mobile unit 445 reports a malfunction or a failure to attach a teat cup, management unit 470 may command mobile unit 444 to "fill in" for mobile unit 443, e.g., attach a teat cup that, per a previous configuration, was to be attached by mobile unit 443.

As described herein, a system and method according to embodiments of the invention may include a mobile unit adapted to travel on a ramp, e.g., a ramp in a milking parlor (or parlor). For example, in an embodiment, a mobile unit (e.g., mobile unit 140) can travel between the legs of a cow in a stall and park itself below the cow. The mobile unit may then perform any operation as described herein, e.g., attach a milking unit, wash or disinfect the udder of the cow etc.

In an embodiment, the ramp may be a round, rotating ramp or platform. In an embodiment, the ramp includes a holder for a milking equipment unit. A holder may be located as close as possible to a cow in a stall such that the distance from the holder to an udder of a cow in the stall is minimal. Accordingly, when a mobile unit is parked under the cow, an arm of the mobile unit may only need to extend to relatively short distances in order to fetch a milking unit from a holder and attach the milking unit to the cow.

In an embodiment, mobile units may collaborate or cooperate to perform a task. For example, an exemplary task may be attaching four teat cups of a milking unit to a cow. To complete the exemplary task, a first mobile unit (e.g., mobile unit 442) may attach a first teat cup, a second mobile unit (e.g., mobile unit 443) may attach a second teat cup and so on.

A plurality of mobile units may dynamically cause at least some of the mobile units to each perform a portion of a treatment. For example, if mobile unit 442 failed to attach the first teat cup it may (e.g., using its Rx/Tx unit 335) inform mobile unit 443 of the failure and mobile unit 443 may attach the first teat cup and a second teat cup. Accordingly, a mobile unit may be adapted to automatically complete an action which at least one other mobile unit failed to complete.

As discussed, mobile unit 447 may be informed by any other mobile unit in system 400 of a failure to complete a task and may perform the task. For example, mobile unit 447 may attach a teat cup which mobile unit 446 failed to attach. In an embodiment, central management unit 470 may dynamically or automatically allocate tasks. For example, each of mobile units 415, 442, 443, 444, 445, 446 and 447 may report to management unit 470 upon successful completion of a task and/or upon failure to complete a task. Accordingly, management unit 470 may be aware of progress of a task and may allocate or re-allocate sub-tasks to mobile units. For example, a task that includes four sub-tasks may be attaching four teat cups to a cow where attaching any one of the four teat cups is a sub-task. In such exemplary task, management unit 470 may dynamically cause any of mobile units 443, 444,445, 446 and 447 to attach one or more teat cups.

A movement of a mobile unit from one stall to another may be synchronized or based on a movement of another mobile unit. For example, when mobile unit has finished washing the cow in its current stall it may move to the next stall and inform mobile unit 443 that it may move to the stall which mobile unit 442 just left. In another embodiment, mobile unit 442 reports to management unit 470 that it has finished its tasks in the current stall and may request permission from management unit 470 to move to the next stall. Management unit 470 may keep track of the location of all mobile units in system 400 (e.g., based on reports from the mobile units as described). Accordingly, management unit 470 may determine whether or not a mobile unit may move to the next stall (e.g., by determining no other mobile unit is present in the next stall).

Mobile units and management unit 470 may share information. For example, an image taken by mobile unit 442 (that may be the first unit to treat a cow in a milking session) may be shared by all mobile units in system 400. Data (e.g., coordinates of teats in an udder) determined based on an image taken by one of the mobile units may be shared by all units. For example, management unit 470 may receive an image from mobile unit 442, determine, based on the image, the location of the cow teats with respect to the stall or with respect to a known location within a stall, and provide the coordinates to mobile units 442, 443, 444,445, 446 and 447.

Unless explicitly stated, the method embodiments described herein are not constrained to a particular order or sequence. Additionally, some of the described method embodiments or elements thereof can occur or be performed simultaneously, at the same point in time, or concurrently.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A method of milking dairy livestock having at least one teat, fore legs and hind legs, the method comprising:
 positioning the dairy livestock in a milking stall on an annular rotary driven milking platform comprising a plurality of milking stalls, wherein teat cup holders are coupled to said plurality of milking stalls;
 navigating a mobile unit on the annular rotary driven milking platform to a location between the fore legs and hind legs of the dairy livestock, wherein the mobile unit comprises an arm that includes a gripping unit; and, while the mobile unit is positioned at least partially between the fore legs and hind legs of the dairy livestock:
 extending the arm of the mobile unit such that the gripping unit comes in contact with at least one teat cup initially positioned in the teat cup holder coupled to said milking stall, wherein the at least one teat cup is connected to a main milk line;
 gripping the at least one teat cup by the gripping unit;
 retracting the arm of the mobile unit, such that the at least one teat cup is positioned adjacent to the at least one teat of the dairy live stock;
 attaching the least one teat cup to the at least one teat of the dairy livestock; and
 milking the dairy livestock, such that the milk flows directly from the at least one teat cup to the main milk line;
 wherein the annular rotary driven milking platform translates both the dairy livestock and the mobile unit.

2. The method according to claim 1 further comprising treating the dairy livestock with a plurality of mobile units that communicate with one another.

3. The method according to claim 2, wherein any two mobile units communicate directly with one another, communicate with one another via a central control unit, or both.

4. The method according to claim 2, wherein any one of the mobile units is designated to perform a different treatment.

5. The method according to claim 2, wherein a first mobile unit is designated to perform all necessary treatments on a first dairy livestock, and wherein a second mobile unit is designated to perform all necessary treatments on a second dairy livestock.

* * * * *